United States Patent
Goede et al.

(10) Patent No.: US 7,985,766 B2
(45) Date of Patent: Jul. 26, 2011

(54) COMBINATION OF ANTICHOLINERIC AND β MIMETICS FOR THE TREATMENT OF RESPIRATORY DISEASES

(75) Inventors: Joachim Goede, Hanau (DE); Joachim Maus, Muhlheim (DE); Peter Jurgen Cnota, Bad Homburg (DE); Istvan Szelenyi, Schwaig (DE)

(73) Assignee: MEDA Pharma GmbH & Co. KG, Bad Homburg (DE)

( * ) Notice: Subject to any disclaimer, the term of this patent is extended or adjusted under 35 U.S.C. 154(b) by 812 days.

(21) Appl. No.: 11/882,109

(22) Filed: Jul. 30, 2007

(65) Prior Publication Data

US 2007/0270481 A1 Nov. 22, 2007

Related U.S. Application Data

(63) Continuation of application No. 11/483,693, filed on Jul. 11, 2006, now abandoned, which is a continuation of application No. 11/051,469, filed on Feb. 7, 2005, now abandoned.

(60) Provisional application No. 60/541,957, filed on Feb. 6, 2004.

(51) Int. Cl.
 *A61K 31/4015* (2006.01)
 *A61K 31/167* (2006.01)
(52) U.S. Cl. .................................... 514/424; 514/630
(58) Field of Classification Search .................. None
 See application file for complete search history.

(56) References Cited

U.S. PATENT DOCUMENTS

| | | |
|---|---|---|
| 6,475,467 B1 | 11/2002 | Keller et al. |
| 6,645,466 B1 | 11/2003 | Keller et al. |
| 2001/0027789 A1 | 10/2001 | Goede et al. |
| 2002/0115681 A1 | 8/2002 | Bozung et al. |
| 2002/0151597 A1 | 10/2002 | Banerjee et al. |
| 2003/0068280 A1 | 4/2003 | Bannister et al. |
| 2004/0002548 A1 | 1/2004 | Bozung et al. |

FOREIGN PATENT DOCUMENTS

| | | |
|---|---|---|
| WO | WO 01/76575 A2 | 10/2001 |
| WO | WO 02/078671 A1 | 10/2002 |

*Primary Examiner* — Phyllis G. Spivack
(74) *Attorney, Agent, or Firm* — Venable LLP; Ann S. Hobbs

(57) ABSTRACT

The present invention describes a combination of an anticholinergic, such as R,R-glycopyrrolate, and a β mimetic, such as tormoterol, for the treatment of respiratory diseases including airway inflammation or obstruction such as chronic obstructive pulmonary disease (COPD) and asthma.

7 Claims, No Drawings

COMBINATION OF ANTICHOLINERIC AND β MIMETICS FOR THE TREATMENT OF RESPIRATORY DISEASES

This application is a continuation of U.S. application Ser. No. 11/483,693, filed Jul. 11, 2006, which is a continuation of U.S. application Ser. No. 11/051,469, filed Feb. 7, 2005, which claims priority to Provisional Application Ser. No. 60/541,957, filed Feb. 6, 2004, the entire contents of each of which are incorporated herein by reference.

The present invention describes a combination of anticholinergic and β mimetics for the treatment of respiratory diseases including airway inflammation or obstruction such as chronic obstructive pulmonary disease (COPD) and asthma. It further comprises the preparation of this combination in a locally applied (inhaled) formulation and application in an inhalation device for instance in the Novolizer®.

It is state of the art that various β-mimetics and anticholinergics can successfully be used as bronchospasmolytics for the treatment of obstructive respiratory ailments, such as COPD and asthma. Substances with β-sympathomimetic effectiveness, such as formoterol or salmeterol are known to be associated with undesirable side-effects in human treatment. In general, the central effects manifest as unease, excitation, sleeplessness, fear, shaking fingers, outbreak of sweating and headache. Here, inhalative application does not exclude these side-effects although they are generally less severe than with peroral or parenteral application. β-sympathomimetics are primarily associated with a more or less pronounced β-stimulating effect on the heart. It generates tachycardia, palpitation, angina pectoris-like complaints and arrhythmia.

Anticholinergic agents such as glycopyrrolate prevent the effects resulting from passage of impulses through the parasympathetic nerves. This action results from their ability to inhibit the action of the neurotransmitter acetylcholine by blocking its binding to muscarinic cholinergic receptors. There are at least three types of muscarinic receptor subtypes. M1 receptors are found primarily in brain and other tissue of the central nervous system, M2 receptors are found in heart and other cardiovascular tissue, and M3 receptors are found in smooth muscle and glandular tissues. The muscarinic receptors are located at neuroeffector on, e.g. smooth muscle and, in particular, M3 muscarinic receptors are located in airway smooth muscle. Consequently, anticholinergic agents may also be referred to as muscarinic receptor antagonists.

The parasympathetic nervous system plays a major role in regulation bronchomotor tone, and bronchoconstriction is largely the result of reflex increases in parasympathetic activity caused in turn by a diverse set of stimuli.

There are muscarinic receptors on peripheral systems such as salivary glands and gut and therefore the use of systemically active muscarinic receptor antagonists is limited by side-effects such as dry mouth and constipation. Thus the bronchodilatory and other beneficial actions of muscarinic receptor antagonists are ideally produced by an inhaled agent which has a high therapeutic index for activity in the lung compared with the peripheral compartment.

Anticholinergic agents also partially antagonize bronchoconstriction induced by histamine, bradykinin, or prostaglandin F2alpha, which is deemed to reflect the participation of parasympathetic efferents in the bronchial reflexes elicited by these agents.

It is well accepted that the stimulation of β2-adrenergic receptors stimulates adenylate cyclase resulting in an increased level of the second messenger cAMP that in turn leads decreased intracellular calcium concentration and consequently smooth muscle relaxation. Stimulation of M3 receptors causes hydrolysis of polyphosphoinositides and mobilization of intracellular calcium which results in a variety of $Ca^{2+}$-mediated responses such as smooth muscle contraction. Consequently, inhibition of this receptor activation prevents the intracellular calcium increase and leads to smooth muscle relaxation.

As the current treatment of asthma and COPD is not satisfactory improved, the problem underlying the present invention was to provide effective and more convenient therapeutic interventions.

A solution is given by the combination of a β-sympathomimetic, which has a long-lasting effect, with an anticholinergic, which has a long-lasting effect.

Due to their different mode of action, the combination of anticholinergic and β-sympathomimetic agents is reasonable, but surprisingly, it has now been found that the above mentioned side-effects can be substantially reduced. In addition, it was also very surprisingly discovered that the bronchospasmolytic effects of the anticholinergic, which has a long-lasting effect, and the β-mimetic, which has a long-lasting effect, increase in a superadditive manner with the combination of active ingredients. According to the invention, a substantial increase in effectiveness can be expected—in comparison to the individual substances and combinations known from prior art—in the case of both COPD and asthma. In a further aspect, this combination therapy exhibits both a fast onset of action and a prolonged duration of action, so that patients feel a rapid improvement in their condition and, in view of the duration of action, a reduced need for short-acting rescue medicaments, such as salbutamol or terbutaline. Surprisingly this effect is exhibited when the two drugs are administered at the same time, i.e. in a composition containing both drugs or sequentially. Therefore, medicaments of the invention facilitate the treatment of inflammatory or obstructive airway diseases because a once daily therapy may be sufficient. Where necessary, medicaments of the invention can be used on demand in rescue treatment of obstructive or inflammatory airway diseases, so that they facilitate treatment of such diseases with a single medicament.

Experimental Part

The interaction between formoterol and R,R-glycopyrrolate was investigated in anesthetized (urethane 2 mg/kg, intraperitoneally) male guinea pigs weighing 400-600 g. After cannulating the trachea, animals were respired using a small animal respiratory pump with a constant tidal volume and a rate of 60 breaths/min. The lung resistance was measured by using a rodent lung function recording system (MUMED, London, UK). Compounds were given intravenously (i.v.) via a catheter placed in the right jugular vein. After surgery, the animals were allowed to stabilize. 10 min before acetylcholine (10 µg/kg, i.v.) administration, the guinea pigs were disconnected from the respirator and either vehicle (10 mg/lactose) or different amounts of drugs (blended with lactose) were administered intratracheally (i.th.) using a syringe. The trachea was then reconnected to the respirator and changes in pulmonary mechanics were recorded. Acetylcholine (10 µg/kg) was injected intravenously in every 10 minutes for 60 min.

Acetylcholine administered i.v. caused a sustainable, three to four-fold increase in the pulmonary resistance. Both R,R-glycopyrrolate and formoterol dose-dependently inhibited the acetylcholine-induced bronchoconstriction. R,R-glycopyrrolate was not effective at the dose of 1 µg/kg, i.th., but it inhibited the bronchospasm by ca. 40% at 3 µg/kg, i.th. and by about 80% at 10 µg/kg, i.th., respectively. Similarly, formoterol did not show any bronchodilatory effects at the lowest dose of 1 μg/kg, i.th., but it slightly dilated the airways at the medium dose of 3 mg/kg, i.th. (about 20%). At the highest dose of 10 μg/kg, i.th. formoterol almost completely attenuated bronchoconstriction induced by i.v. acetylcholine. When applying R,R-glycopyrrolate and formoterol each at the dose of 1 μg/kg, i.th., together, the simultaneous administration resulted in an almost complete attenuation of acetylcholine-induced bronchoconstriction. Surprisingly, the two compounds given in doses which alone were not effective at all, led, when administered simultaneously, to a very strong bronchodilatory effect in guinea pigs clearly indicating the overadditive nature of this interaction.

The types of diseases that may be treated using the combinations of the present invention include, but are not limited to, asthma, chronic or acute bronchoconstriction, chronic bronchitis, airway obstruction, emphysema, chronic obstructive pulmonary disease (COPD), COPD that has chronic bronchitis, pulmonary emphysema or dyspnea associated therewith and COPD that is characterized by irreversible, progressive airway obstruction, and exacerbation of airway reactivity consequent to other drug therapy, e.g., aspirin therapy. In one aspect, the present invention provides a medicament containing, separately or together, (A) formoterol or salmeterol, or a pharmaceutically acceptable salts thereof or a solvate of formoterol/salmeterol or said salts and (B) racemic glycopyrrolate, one of its enantiomers, especially of (R,R)-glycopyrrolate, one of its diastereoisomers, or its pharmaceutically acceptable salts, for simultaneous, sequential or separate administration in the treatment of respiratory diseases, especially inflammatory or obstructive diseases. In another aspect, the present invention provides a method of treating a respiratory, especially inflammatory or obstructive disease which comprises administering to a subject in need of such treatment effective amounts of (A) as herein before defined and (B) as herein before defined.

In a further aspect, the present invention provides a pharmaceutical composition comprising a mixture of effective amounts of (A) as herein before defined and (B) as herein before defined, optionally together with a pharmaceutically acceptable carrier.

The present invention also provides (A) and (B) as herein before defined in combination therapy by simultaneous, sequential, or separate administration in the treatment of respiratory diseases.

The invention further provides the use of (A) as herein before defined or (B) as herein before defined in the preparation of a medicament for combination therapy by simultaneous, sequential, or separate administration of (A) and (B) in the treatment of respiratory diseases. The present invention still further provides the use of (A) and (B) as herein before defined for the preparation of a medicament for combination therapy by simultaneous, sequential, or separate administration in the treatment of respiratory diseases.

Pharmaceutically acceptable salts of formoterol or salmeterol include, for example, salts of inorganic acids such as hydrochloric, hydrobromic, sulfuric and phosphoric acids, and organic acids such as fumaric, maleic, acetic, lactic, citric, tartaric, ascorbic, succinic, glutaric, gluconic, tricarballylic, oleic, benzoic, p-methoxybenzoic, salicylic, o-and p-hydroxybenzoic, p-chlorobenzoic, methanesulfonic, p-toluenesulfonic and 3-hydroxy-2-naphthalene carboxylic acids.

Component (A) may be in any isomeric form or mixture of isomeric forms, for example a pure enantiomer, a mixture of enantiomers, a racemate or a mixture thereof. It may be in the form of a solvate, for example a hydrate, thereof, for example a pure enantiomer, a mixture of enatiomers, a racemate or a mixture thereof. It may be in the form of a solvate, for example a hydrate, thereof, and may be present in a particular crystalline form. Preferably, component (A) is formoterol fumarate, especially in the form of the dihydrate or is salmeterol xinafoate, especially in the form of the pure salt but also in the form of a solvate, for example a monohydrate or a dihydrate.

Administration of the medicament or pharmaceutical composition as herein before described, with (A) and (B) in admixture or separate, is preferably by inhalation, i.e. (A) and (B) or the mixture thereof are in inhalable form. The inhalable form of the medicament of (A) (B) may be, for example, an atomizable composition such as an aerosol comprising the active ingredient, (A) and (B) separately or in admixture, in solution or dispersion in a propellant, or a nebulizable composition comprising a dispersion of the active ingredient in an aqueous/organic or medium. For example, the inhalable form of the medicament may be an aerosol comprising a mixture of (A) and (B) in solution or dispersion in a, propellant, or a combination of an aerosol containing (A) in solution or dispersion in a propellant with an aerosol containing (B) in solution or dispersion in a propellant. In another example, the inhalable form is a nebulized composition comprising a dispersion of (A) and (B) in an aqueous or organic medium, or a combination of a dispersion of (A) in such a medium with a dispersion of (B) in such a medium.

In another embodiment of the invention, the inhalable form is a dry powder, i.e. (A) and/or (B) are present in a dry powder comprising finely divided (A) and/or (B) optionally together with a finely divided pharmaceutically acceptable carrier, which is preferably present and may be chosen from materials known as carriers in dry powder inhalation compositions, for example saccharides, including monosaccharides, disaccharides, polysaccharides and sugar alcohols such as arabinose, fructose, ribose, mannose, sucrose, trehalose, lactose, starches, dextran or mannitol. An especially preferred carrier is lactose. The dry powder may be in capsules of gelatin or plastic, or in blisters, for in a dry powder inhalation device. Alternatively, the dry powder may be contained as a reservoir in a dose dry powder inhalation device.

In the finely divided particulate form of the medicament, and in the aerosol composition where the active ingredient is present in particulate form, the active ingredient may have an average particle diameter of up to 4 μm. The finely divided carrier, where present, generally has a maximum diameter up to approximately 500 μm and conveniently has a mean particle diameter of 10 to 350 μm, preferably approx. 110 to 290 μm. The particle size of the active ingredient, and that of the carrier where present in dry powder compositions, can be reduced to the desired level by conventional methods, for example by grinding in an air-jet mill, ball mill or vibrator mill, microprecipitation, spray-drying, lyophilisation or recrystallisation from supercritical media.

The inhalable medicament may be administered using an inhalation device for the inhalable form, such devices being well known in the art. Accordingly, the invention also provides a pharmaceutical product comprising a medicament or pharmaceutical composition as herein before described in inhalable form as herein before described in association with one or more inhalation devices. In a further aspect, the invention provides an inhalation device, or a pack of two or more inhalation devices, containing a medicament or pharmaceutical composition as herein before described in inhalable form as herein before described.

A suitable daily dose of formoterol, or salt or thereof, particularly as formoterol fumarate dihydrate, for inhalation may be from 1 to 72 µg, generally from 3 to 50 µg, preferably from 6 to 48 µg, for instance from 6 to 24 µg.

A suitable daily dose of salmeterol, or salt or thereof, particularly as salmeterol xinafoate, for inhalation may be from 10 to 300 µg, generally from 25 to 200 µg, preferably from 50 to 200 µg, for instance from 50 to 100 µg.

A suitable daily dose of glycopyrrolate salt, particularly as (R,R)-glycopyrrolate, for inhalation may be from 5 to 500 µg, preferably from 15 to 300 µg. A dosage range between 5 and 100 µg/day is especially preferred.

The precise doses used will of depend on the condition to be treated, the patient and the efficiency of the inhalation device. The unit doses of (A) and (B) and their frequency of administration may be chosen accordingly.

In accordance with the above, the invention also provides a pharmaceutical kit comprising (A) and (B) as herein before defined in separate unit dosage forms, said forms being suitable for administration of (A) and (B) in effective amounts. Such a kit suitably further comprises one or more inhalation devices for administration of (A) and (B). For example, the kit may comprise one or more dry powder inhalation devices adapted to deliver dry powder from a capsule, together with capsules containing a dry powder comprising a dosage unit of (A) and capsules containing a dry powder comprising a dosage unit of (B). In another example, the kit may comprise a multidose dry powder inhalation device containing in the reservoir thereof a dry powder comprising (A) and a multi-dose dry powder inhalation device containing in the reservoir thereof a dry powder comprising (B). In a further example, the kit may comprise a metered dose inhaler containing an aerosol comprising (A) in a propellant and a metered dose inhaler containing an aerosol comprising (B) in a propellant.

Treatment of inflammatory or obstructive airway diseases in accordance with the invention may be symptomatic or prophylactic treatment. Inflammatory or obstructive airway diseases to which the present invention is applicable include asthma of whatever type or genesis including both intrinsic non-allergic asthma and extrinsic (allergic) asthma.

The invention is illustrated by but not restricted to the following two examples.

EXAMPLE 1

Powder Inhalation with 12 µg Formoterol Fumarate Dihydrate and 120 µg R,R-glycopyrrolate Per Single Dose A quantity of 12 g micronized formoterol fumarate dihydrate is mixed with 100 g alpha lactose monohydrate, the mixture is given on a sieve of 0.5 mm mesh size and finally mixed again. 120 µg micronized R,R-glycopyrrolate is mixed with 1000 g alpha lactose monohydrate, the mixture is given on a sieve of 0.8 mm mesh size and finally mixed again. The two mixtures received are blended and filled up with alpha lactose monohydrate to 12000 g. Subsequently, it is mixed again and the powder mixture received is filled in powder inhalers releasing 12 mg of powder per single dose. Per single dose, 12 µg formoterol fumarate dihydrate and 120 µg R,R-glycopyrrolate are released from a powder inhaler and supplied to the patient's airways.

EXAMPLE 2

Dosage Aerosol with 6 µg Formoterol Fumarate Dihydrate and 350 µg R,R-glycopyrrolate Per Single Dose A quantity of 1000 g 1,1,1,2,3,3,3 heptafluoropropane (=HFA 227) is cooled down at a temperature of −55° C. and, while stirring, mixed with a solution of 11.7 g polyoxethylene-25-glyceryl-trioleate (trade name: Tagat TO) in 11.7 g absolute ethanol. Subsequently, 0.1008 g micronized formoterol fumarate dihydrate and 5.88 g micronized R,R-glycopyrrolate as well as 0.9 g micronized saccharin sodium is added, and the suspension produced is intensively homogenized. While further cooling and stirring, the suspension is filled up with refrigerated propellant 227 to 1170 g and after mixing again filled in metal cans which are closed with metering valves releasing 50 µl of the suspension per actuation. Thus, 6 µg formoterol fumarate dihydrate and 350 µg R,R-glycopyrrolate are released per actuation.

The invention claimed is:

1. A method for the treatment of chronic obstructive pulmonary disease (COPD) or asthma in a patient suffering from COPD or asthma comprising administration of a combination of R,R-glycopyrrolate and formoterol or physiologically acceptable salt(s) thereof.

2. The method of claim 1 wherein the daily dose of R,R-glycopyrrolate is between 5 and 500 µg.

3. The method of claim 1 wherein the daily dose of formoterol is between 200 and 5,000 µg.

4. The method of claim 1 wherein the combination is administered in an inhalable aerosol.

5. The method of claim 1 wherein the combination is administered in an inhalable dry powder.

6. The method of claim 1 wherein the R,R-glycopyrrolate and formoterol are presented in fixed or free combination for simultaneous, sequential or separate administration, optionally together with a suitable excipient, adjunct or additive in a pharmaceutical form suitable for inhalative application.

7. The method of claim 1 wherein the patient is a human or horse.

* * * * *